United States Patent
Urisu et al.

(10) Patent No.: US 10,208,284 B2
(45) Date of Patent: Feb. 19, 2019

(54) CELL-SEEDING AND -CULTURING DEVICE

(71) Applicant: Japan Science and Technology Agency, Saitama (JP)

(72) Inventors: Tsuneo Urisu, Aichi (JP); Zhi-hong Wang, Aichi (JP); Hidetaka Uno, Aichi (JP); Yasutaka Nagaoka, Aichi (JP)

(73) Assignee: JAPAN SCIENCE AND TECHNOLOGY AGENCY, Saitama (JP)

( * ) Notice: Subject to any disclaimer, the term of this patent is extended or adjusted under 35 U.S.C. 154(b) by 131 days.

(21) Appl. No.: 15/113,153

(22) PCT Filed: Jan. 23, 2015

(86) PCT No.: PCT/JP2015/051905
§ 371 (c)(1),
(2) Date: Jul. 21, 2016

(87) PCT Pub. No.: WO2015/111722
PCT Pub. Date: Jul. 30, 2015

(65) Prior Publication Data
US 2017/0002315 A1  Jan. 5, 2017

(30) Foreign Application Priority Data
Jan. 24, 2014 (JP) .................. 2014-011640

(51) Int. Cl.
*C12M 1/00* (2006.01)
*C12N 5/079* (2010.01)
(Continued)

(52) U.S. Cl.
CPC .......... *C12N 5/0618* (2013.01); *C12M 23/16* (2013.01); *C12M 25/06* (2013.01); *C12M 33/06* (2013.01)

(58) Field of Classification Search
CPC ..................................... C12M 23/16
(Continued)

(56) References Cited

U.S. PATENT DOCUMENTS

2005/0279634 A1   12/2005  Ozaki et al.
2010/0203621 A1*  8/2010   Takahashi ........ G01N 33/48728
                                                          435/287.1
(Continued)

FOREIGN PATENT DOCUMENTS

EP       2037258 A1      3/2009
JP    2003-088357 A      3/2003
(Continued)

OTHER PUBLICATIONS

Erickson et al., "Caged neuron MEA: A system for long-term investigation of cultured neural network connectivity," Journal of neuroscience Methods, vol. 175, 2008, pp. 1-16.
(Continued)

*Primary Examiner* — Kevin Joyner
*Assistant Examiner* — Holly M Mull
(74) *Attorney, Agent, or Firm* — Kilpatrick Townsend & Stockton LLP

(57) ABSTRACT

Provided is a device for seeding cells in a plurality of cell arrangement areas in a simple manner and a short period of time. A seeding and culturing device (1) for cells capable of forming a nerve network, the device comprising a cell-culturing substrate (2) having a plurality of cell arrangement areas (8) enclosed by a plurality of projecting parts, and a flow channel substrate (3) arranged on the cell-cultivating substrate (2) and having a plurality of through-holes (14), wherein the through-holes (14) are configured so as to provide flow channels in which the upper surface side of the substrate is an entrance (15) and the lower surface side of the
(Continued)

substrate is an exit, and the exit (16) of the flow channels is positioned above any of the cell arrangement areas.

12 Claims, 9 Drawing Sheets

(51) Int. Cl.
*C12M 1/12* (2006.01)
*C12N 13/00* (2006.01)
*C12M 1/32* (2006.01)
*C12M 3/06* (2006.01)

(58) Field of Classification Search
USPC .................................................. 435/289.1
See application file for complete search history.

(56) References Cited

U.S. PATENT DOCUMENTS

| | | | |
|---|---|---|---|
| 2011/0229961 A1 | 9/2011 | Higashi et al. | |
| 2013/0189671 A1* | 7/2013 | Hoh .................. | C12M 23/16 435/3 |
| 2014/0190830 A1* | 7/2014 | Sturmer ............ | B01L 3/502792 204/452 |
| 2014/0339102 A1 | 11/2014 | Urisu et al. | |
| 2015/0233890 A1 | 8/2015 | Urisu et al. | |

FOREIGN PATENT DOCUMENTS

| | | |
|---|---|---|
| JP | 2009-124968 A | 6/2009 |
| JP | 2009-131240 A | 6/2009 |
| JP | 2009-204407 A | 9/2009 |
| JP | 2013-146261 A | 8/2013 |
| WO | 2005/001018 A1 | 1/2005 |
| WO | 2007/116978 A1 | 10/2007 |
| WO | 2013/094418 A1 | 6/2013 |
| WO | 2014/045618 A1 | 3/2014 |

OTHER PUBLICATIONS

Goto-Saitoh et al., "Control of the neuronal cell migration by incubation substrate with cell cage pattern," the 74th JSAP Autumn Meeting, 2013 Koen Yokoshu, Aug. 31, 2013, pp. 12-150.

Tan et al., "A trap-and-release integrated microfluidic system for dynamic microarray applications," PNAS, vol. 104, No. 4, Jan. 23, 2007, pp. 1146-1151.

Wang et al., "Positioning of the sensor cell on the sensing area using cell trapping pattern in incubation type planar patch clamp biosensor," Colloids and Surfaces B: BioInterfaces, vol. 96, 2012, pp. 44-49.

Zeck et al., "Noninvasive neuroelectronic interfacing with synaptically connected snail neurons immobilized on a semiconductor chip," Proceedings of the National Academy of Sciences of USA, 2001, vol. 98, No. 18, pp. 10457-10462.

PCT/JP2015/051905, International Search Report, dated Apr. 28, 2015, 2 pages.

European Application No. 15740083.9, Extended European Search Report, dated Aug. 11, 2017, 2 pages.

\* cited by examiner

FIG. 9
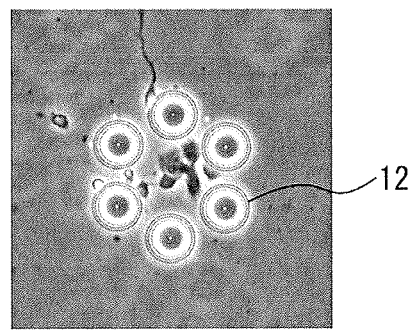
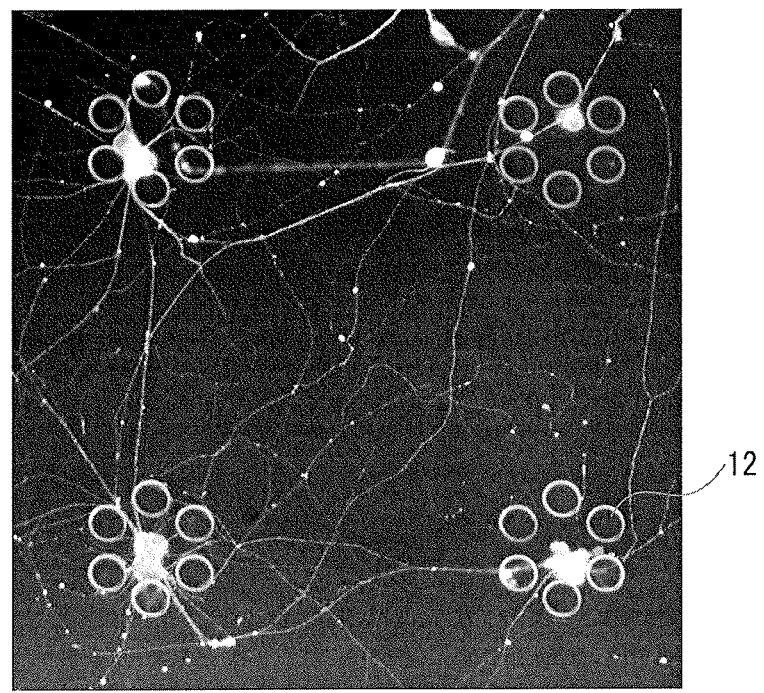

CELL-SEEDING AND -CULTURING DEVICE

CROSS-REFERENCE TO RELATED APPLICATIONS

This application is a 371 National Phase Application of PCT/JP2015/051905, filed Jan. 23, 2015, which application claims priority to JP 2014-011640, filed Jan. 1, 2014, the disclosures all of which are incorporated herein by reference.

TECHNICAL FIELD

The present invention relates to a cell seeding and culturing device capable of arranging cells in a plurality of cell arrangement areas.

BACKGROUND ART

Research has recently become increasing active in the area of intercellular networks, and proposals have been made for constructing intercellular networks in vitro. Cell networks that have been constructed in vitro are useful in imaging research and electrophysiological research using the patch-clamp method. In order to construct an intercellular network in vitro, it is necessary to culture cells arranged at prescribed locations. For example, in Non-Patent Document 1, an experiment was conducted to detect the electrical potential of nerve cells by providing a region surrounded by a plurality of projections on a silicon substrate having a transistor arranged thereon, and arranging peripheral nerve cells of Lymnaea stagnalis in the form of large ganglia thereon. In addition, Non-Patent Document 2 discloses a neurochip obtained by forming a plurality of roughly disk-shaped enclosures referred to as "cages" on a substrate, arranging nerve cells in a space in the center of the cages, and allowing axons of the nerve cells to extend through several tunnels provided in the cages towards nerve cells in adjacent cages. However, Non-Patent Documents 1 and 2 do not disclose nerve cell seeding systems for efficiently seeding nerve cells in a large number of cell establishment areas. Methods involving the manual seeding of cells in individual cell arrangement areas using equipment such as ordinary pipettes, pipettes equipped with a measuring function or micro-injectors make it difficult to accurately seed cells in extremely minute cell arrangement areas, thereby resulting in inferior seeding efficiency and making these methods undesirable.

On the other hand, the patch-clamp method is an electrophysiological technique for examining signal transduction between cells by measuring membrane potential and membrane current, and is carried out using ordinary pipettes. However, in the case of the pipette patch-clamp method, since the technique involves capturing (clamping) individual cells with a pipette followed by measuring their electrical changes, it is unable to accommodate high-throughput screening by multi-point measurement. The inventors of the present invention developed a planar patch-clamp method for the purpose of using the patch-clamp method for high-throughput screening (Patent Documents 1 and 2). This planar patch-clamp method consists of providing a plurality of microscopic through holes in an electrically insulated substrate and then measuring electrical changes, such as changes in membrane potential or membrane current, in cells arranged on these through holes, thereby enabling high-throughput screening by multi-point measurement. However, in order to construct an intercellular network in vitro, similar to the difficulty encountered in seeding cells into a large number of cell establishment areas, the difficulty remained in accurately arranging cells on a plurality of the through-holes in the electrically insulated substrate.

Thus, in order to construct an intercellular network in vitro, it is additionally required to be able to accurately and rapidly arrange cells in prescribed arrangement areas in order to study electrical properties using the planar patch-clamp method.

In addition to methods using pipettes, an automated cell seeding method that mechanically automates a cell seeding method using pipettes by utilizing the principle of an inkjet printer has been developed for use as a technology for seeding cells in prescribed cell arrangement areas (Patent Document 3). In addition, as another example of a technology for cell seeding, a technology has been implemented for seeding cells based on the principle of embedding cells in sequential cell arrangement areas in the form of depressions by transporting cells to a prescribed depression using microchannels and then transporting the cells to the next depression when that depression has been filled (Non-Patent Document 3).

PRIOR ART DOCUMENTS

Patent Documents

Patent Document 1: Japanese Unexamined Patent Publication No. 2009-204407
Patent Document 2: Japanese Unexamined Patent Publication No. 2013-146261
Patent Document 3: Japanese Unexamined Patent Publication No. 2009-131240
Patent Document 4: International Publication No. WO 2013/094418

Non-Patent Documents

Non-Patent Document 1: G. Zeck, et al., PNAS 98 (2001), 10457-10462
Non-Patent Document 2: J. Erickson, et al., J. Neurosci. Methods, 175 (2008), 1-16
Non-Patent Document 3: W. H. Tan, et al., PNAS 104 (2007), 1146-1151

DISCLOSURE OF THE INVENTION

Problems to be Solved by the Invention

The inventors of the present invention found that the following problems occur when using a conventional cell seeding method in an attempt to form a complex and sophisticated in vitro cell network based on the premise of applying the method to high-throughput screening and the planar patch-clamp method.

1. In the case of a cell seeding method that uses pipettes, there is the problem of being unable to seed cells in a large number of cell arrangement areas in a short period of time, and the cells end up dying due to the large amount of time required for seeding.

2. In the case of a cell seeding method using the principle of an inkjet printer, although this method requires that depressions be formed in cell arrangement areas and that cells be established in those depressions, if the depth of the depressions is not sufficiently deep in comparison with the thickness of the cells, the cells end up protruding from the arrangement areas and are unable to be seeded at the correct locations, while as a result of the depressions being excessively deep, the problem occurs of it being difficult to form an intercellular network.

3. Similarly in the case of a cell seeding method that uses microchannels, since the cells are arranged in depressions, there is the problem of it being difficult to form an intercellular network.

Thus, there continues to be a desire for the development of a device that allows cells to be seeded in a plurality of cell arrangement areas easily and accurately and in a short period of time. Since a cell network is formed after seeding the cells in cell arrangement areas, the seeding device is required to be configured so as to not impede the formation of a cell network after seeding.

Means for Solving the Problems

As a result of conducting extensive studies with the foregoing problems in view, the inventors of the present invention found that the aforementioned problems can be solved by devising a cell seeding and culturing device comprising a cell culturing substrate capable of forming a nerve cell network that has a plurality of cell arrangement areas surrounded by a plurality of projections, and a flow channel substrate having a plurality of through holes, wherein each of the through holes is arranged at locations above the cell arrangement areas.

Thus, the present invention relates to the inventions indicated below.

[1] A cell seeding and culturing device capable of forming a nerve cell network, comprising a cell culturing substrate which enables a nerve cell to form network, and which has a plurality of cell arrangement areas surrounded by a plurality of projections, and a flow channel substrate having a plurality of through holes, and being arranged on the culturing substrate, wherein each of the through holes defines a flow channel, wherein the upper side of the substrate is an entrance and the lower side of the substrate is an exit, and the exit of each flow channel is located above the cell arrangement areas.

[2] The cell seeding and culturing device described in [1], wherein a spacer member having a thickness greater than the height of the projections is arranged between the culturing substrate and the flow channel substrate.

[3] The cell seeding and culturing device described in [1] or [2], having a gap, capable of forming a nerve cell network between the cell arrangement areas, between the culturing substrate and the flow channel substrate corresponding to the thickness of the spacer member.

[4] The cell seeding and culturing device described in any of [1] to [3], wherein a gap through which cells flow out is not present between the exits of the flow channels and the projections.

[5] The cell seeding and culturing device described in any of [1] to [4], further comprising a liquid storage substrate that defines a liquid storage area on the upper surface of the flow channel substrate.

[6] The cell seeding and culturing device described in any of [1] to [5], wherein the culturing substrate is an electrically insulated substrate used in a planar patch-clamp method, and has through holes for the planar patch-clamp method in the cell arrangement areas that do not allow the passage of cells but allow the attaining of electrical continuity.

[7] The cell seeding and culturing device described in any of [1] to [5], wherein the culturing substrate is an imaging substrate of a nerve cell network.

Effects of the Invention

According to the cell seeding and culturing device of the present invention, cells can be seeded in a plurality of cell arrangement areas accurately and in a short period of time using a simple procedure. Moreover, in the cell seeding and culturing device of the present invention, the ability to form a cell network with the seeded cells is not impeded.

BRIEF DESCRIPTION OF THE DRAWINGS

FIG. 9 shows photographs of (A) cells seeded by the cell seeding and culturing device (1) of the present invention, and (B) a cell network formed thereafter.

BEST MODE FOR CARRYING OUT THE INVENTION

[Cell Seeding and Culturing Device]

Figure 1:
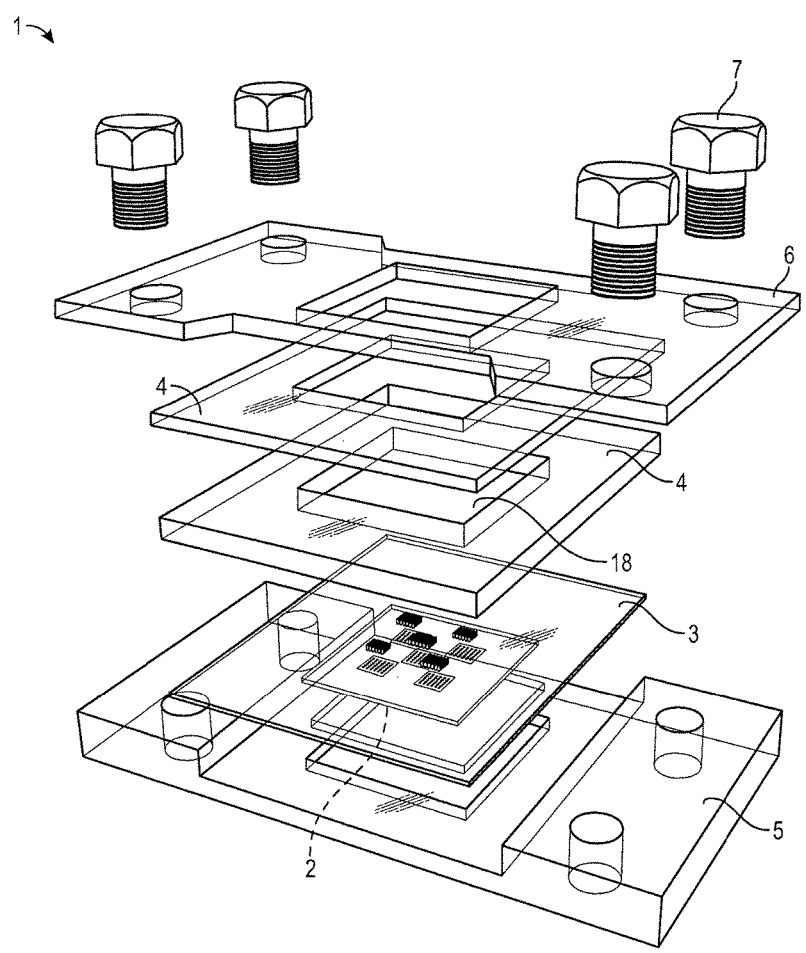
FIG. 1 is an exploded schematic diagram showing one example of a cell seeding and culturing device (1).
Figure 4:
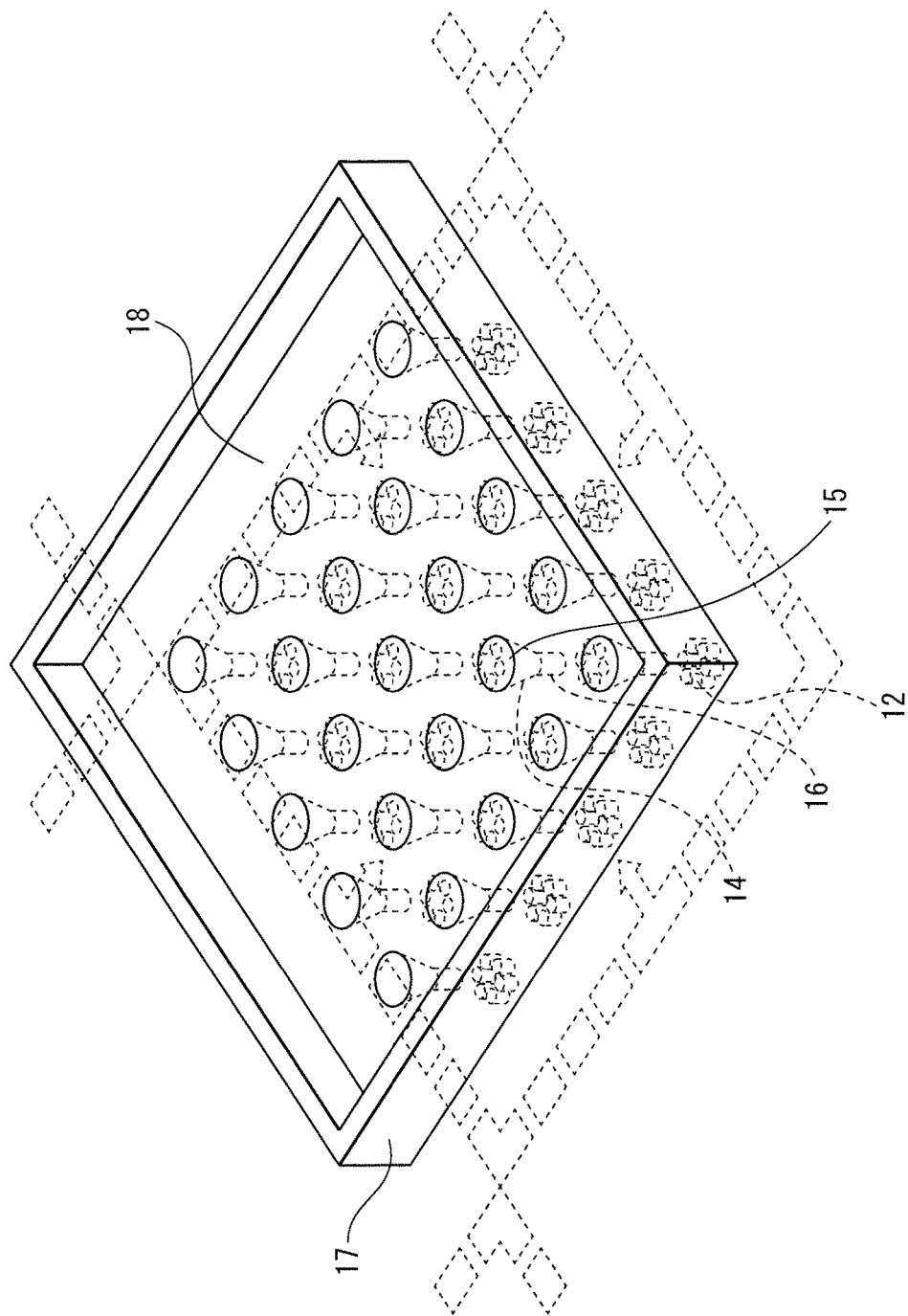
FIG. 4 shows flow channels defined by through holes (14) formed in a flow channel substrate (3).

The cell seeding and culturing device (1) of the present invention comprises a cell culturing substrate (2) having a plurality of cell arrangement areas (8), and a flow channel substrate (3) having a plurality of through holes (14), wherein the flow channel substrate (3) is arranged so that each of the through holes (14) is located above any of the cell arrangement areas (8) (FIG. 1). Each of the through holes (14) opened in the flow channel substrate (3) define flow channels such that the upper surface side of the flow channel substrate (3) is defined as an entrance (15) and the lower surface side of the flow channel substrate (3) is defined as an exit (16), and the exit (16) of each flow channel is configured so as to be located above any of the cell arrangement areas (8) (FIG. 4). In addition to the cell culturing substrate (2) and the flow channel substrate (3), the cell seeding and culturing device (1) may also contain a liquid storage substrate (4) that defines a liquid storage area, and substrate immobilizing substrates that immobilize the substrates. The substrate immobilizing substrates may have any arbitrary form provided they are able to immobilize the substrates to prevent them from moving, and for example, the substrates may be immobilized with a lower substrate immobilizing substrate (5) and an upper substrate immobilizing substrate (6) by interposing those substrates, or with fasteners (7) such as screws or clips.

After having seeded the cell seeding and culturing device (1) with cells, the device is placed as is in a culture vessel such as a Petri dish, bottle or dish containing a culture medium, and cell culturing is carried out until cells have been established in the cell arrangement areas (8). Alternatively, the cells may be seeded with the cell seeding and culturing device (1) initially placed in a culture vessel containing culture medium followed by carrying out cell culturing until the cells become established in the cell arrangement areas (8). After allowing a sufficient amount of time to pass for the cells to become established, the flow channel substrate (3) is removed from the cell seeding and culturing device (1), thereby enabling the cell culturing plate (2) to be used in a subsequent experiment, such as induction of differentiation, promotion of the formation of a cell network or various other experiments performed after forming a cell network. Induction of cell differentiation and promotion of the formation of a cell network may also be carried out prior to removing the flow channel substrate (3).

The cell culturing substrate (2) contains the cell arrangement areas (8) for arranging cells. The plurality of cell arrangement areas (8) contained in the cell culturing substrate (2) may be composed of only a single compartment or may be divided into a plurality of compartments by a spacer member (9). Here, the spacer member (9) is used to simultaneously separate compartments and protect projections and the like present on the cell culturing substrate when placing another substrate on the cell separating substrate. The spacer member (9) may be of the same material or different material as the cell culturing substrate, and although an arbitrary thickness may be selected, the thickness thereof is preferably thicker than the height of the projections. More preferably, an elastic material such as PDMS or silicone rubber can be used for the spacer member (9), and in this case, the thickness of the spacer can be adjusted by adjusting the tightness of the screws (7), thereby making it possible to change the size of a gap (30) between the flow channel exits (16) and cell retainers (10) such as the upper portions of projections (12). As a result, the ratio of the number cells seeded in the cell arrangement areas (8) and the number of cells seeded after escaping outside the cell arrangement areas (8) can be changed during cell seeding. If this gap is zero, namely in the state in which the flow channel exits (16) and the cell retainers (10), such as the upper portions of the projections (12), are pressed together, cells can be prevented from being seeded outside the cell arrangement areas (8) or at least their seeding outside the cell arrangement areas (8) can be avoided as much as possible. As a result of arranging a spacer member having a thickness greater than the height of the projections between the cell culturing substrate (2) and the flow channel substrate (3), a gap corresponding to the thickness of the spacer member can be formed between the cell culturing substrate (2) and the flow channel substrate (3), thereby enabling seeded cells to form a nerve cell network among the cell arrangement areas. A gap corresponding to the thickness of the spacer member corresponds to the total of the height of the projections and the gap (30). If the gap (30) is zero, namely in the state in which flow channel exits (16) and upper portions of the projections (12) are pressed together, a gap corresponding to the height of the projections is formed between the cell culturing substrate (2) and the flow channel substrate (3). The height corresponding to the height of the projections and the gap can also be represented as simply the height of the projections or a height in excess thereof. Although a cell network forms between cell arrangement areas (8) present in the same compartment, cell networks are not formed between cell arrangement areas (8) present in other compartments. The movement of liquid may or may not occur between different compartments. For example, in the case of carrying out imaging research using the cell culturing substrate (2) that has been seeded with cells, imaging is preferably carried out while changing the reagent for each compartment, and it is therefore preferable to employ a configuration that does not permit the flow of liquid to occur in this case. On the other hand, in the case of using the cell culturing substrate (2) that has been seeded with cells in the planar patch-clamp method, flow channels may be connected so as to allow electrical continuity among the compartments from the viewpoint of reducing the number of electrodes on the upper side.

The material of the cell culturing substrate (2) can be selected arbitrarily corresponding to the purpose of use thereof. From the viewpoint of irradiating with a laser from below or observing with a microscope, the cell culturing substrate (2) is preferably a clear substrate, and a glass, ceramic or plastic substrate can be arbitrarily selected. In addition, in the case of using for planar patch-clamp, the material of the cell culturing substrate (2) is required to be electrically insulated and be provided with planar patch-clamp through holes (corresponding to reference number 21 in FIGS. 6 and 7 to be subsequently described). The size of the planar patch-clamp through holes may be of any arbitrary size provided they do not allow the passage of cells but allow electrical continuity, and is, for example, 1 µm to 4 µm. The electrically insulated cell culturing substrate (2) may be formed from a single material or may be formed by mixing or laminating a plurality of materials. Although the thickness of the cell culturing substrate (2) is arbitrary corresponding to the material, from the viewpoints of securing strength and insulating properties, it is 0.1 mm or more, preferably 0.2 mm or more and more preferably 0.5 mm or more. From the viewpoint of forming a thin film region having a thickness of 10 µm to 20 µm by simultaneously embossing both sides, the thickness of the cell culturing substrate (2) is 1.5 mm or less, preferably 1 mm or less and more preferably 0.5 mm or less.

In addition, in order to allow cells to adhere thereto, the cell culturing substrate (2) may be introduced with hydrophilic functional groups by subjecting to hydrophilic treatment such as plasma treatment, or may be coated with an arbitrary adhesive substance referred to as an extracellular matrix, examples of which include polylysine, hyaluronic acid, Matrigel and proteoglycans (such as versican, decorin, aggrecan, chondroitin sulfate or heparan sulfate), an adhesive protein, examples of which include collagen (such as type I, type II or type IV collagen), fibronectin, laminin, link protein, entactin, tenascin, cadherin, elastin, fibrin and gelatin, or partial peptides thereof. This treatment may be carried out only on the cell arrangement areas (8) or on the entire cell culturing substrate (2).

The cell arrangement areas (8) defined by the cell culturing substrate (2) may also have the cell retainers (10) for impeding the movement and outflow of cells. As a result, a cell network can be constructed while restricting the movement of cells. A plurality of the cell arrangement areas (8) is provided on the cell culturing substrate (2) in order to form a cell network. The interval between the cell arrangement areas (8) can be set arbitrarily corresponding to the type of cell network, and in the case of forming a nerve cell network, for example, the cell arrangement areas (8) can be arranged at an interval of about 50 µm to 500 µm.

The cell retainers (10) for retaining cells may be in the form of a plurality of projections (12) capable of retaining cells. In a preferable aspect thereof, the number of cells retained by the cell retainers (10) is one or a plurality of cells, for example 1 to 9 cells, and preferably 1 to 5 cells. The cell arrangement areas (8) defined by the projections (12) are of a size capable of containing one to a plurality of cells, and can be suitably set corresponding to the size of the cells and number of cells desired to be retained. For example, in the case of arranging a single mammalian nerve cell, the inner diameter of the cell retainers (10) is preferably about 10 μm to 25 μm.

The number of the projections (12) may be, for example, 3, 4, 5 or 6 or more since 1 or a plurality of cells are to be retained. The shape of the projections (12) is arbitrary provided one or a plurality of cells can be retained, and examples thereof include a columnar shape and conical shape. The cross-section of each projection (12) may also have an arbitrary shape, and examples thereof include a circle and a polygon such as a triangle, quadrangle, pentagon or hexagon. The projections (12) may be in the form of an apex or palisade that is bridged partway. The interval between the projections (12) as well as the height and number of the projections (12) can be suitably selected corresponding to the type and number of cells to be retained. For example, the interval between the projections (12) can be determined corresponding to the size of a cell body, and when the average size of a cell body is taken to be 15 for example, the upper limit value of the interval between the projections (12) is preferably 10 μm or less and particularly preferably 5 μm or less from the viewpoint of impeding the outflow of cells, while the lower limit value of the interval is preferably 1 μm or more and particularly preferably 1.5 μm or more from the viewpoint of not impeding the formation of a cell network. The height of the projections (12) is preferably 5 μm or more and particularly preferably 10 μm or more from the viewpoint of effectively restricting random movement of cells. On the other hand, the height of the projections (12) is preferably 15 μm or less and particularly preferably 10 μm or less from the viewpoints of preventing layering of cells, coating the inner surfaces of the cell arrangement areas (8) with an extracellular matrix, and retaining a number of cells in the cell retainers (10) suitable for forming a matrix cell network.

The flow channel substrate (3) that composes the cell seeding and culturing device (1) contains a plurality of through holes (14). The flow channel substrate (3) is superimposed on the cell culturing substrate (2), and the surfaces of the flow channel substrate (3) are such that the surface on the side of the cell culturing substrate (2) is defined as the lower surface and the other surface is defined as the upper surface. Each of the through holes (14) formed in the flow channel substrate (3) defines a flow channel in which the upper surface of the flow channel substrate (3) is defined as an entrance (15) and the lower surface of the flow channel substrate is defined as an exit (16). In the case the flow channel substrate is superimposed on the cell culturing substrate (2), the flow channel substrate (3) is configured such that each flow channel exit (16) is located above the cell arrangement areas (8) of the cell culturing substrate (2) or the cell retainers (10). As a result, cells that have passed through a flow channel can be arranged in the cell arrangement areas (8) or cell retainers (10). Although the exits (16) of all of the through holes (14) are preferably configured so as to be located above the cell arrangement areas (8) of the cell culturing substrate (2) or the retainers (10), a portion of the through holes (14) can also be configured so as to arrange cells outside the cell arrangement areas (8) of the cell culturing substrate (2). As a result, cells can be arranged outside the cell arrangement areas (8) while arranging cells within the cell arrangement areas (8). In a more preferable aspect, the flow channels are tapered from the entrances (15) to the exits (16) and have, for example, a funnel shape or conical shape, and as a result thereof, the utilization rate of cells supplied to the upper surface of the flow channel substrate (3) can be enhanced, making this suitable for seeding of small numbers of valuable cells such as nerve cells that have differentiated from ES cells or iPS cells. Although the thickness of the flow channel substrate (3) is arbitrary, in the case of employing a configuration in which the flow channels are tapered from the entrances (15) to the exits (16), the flow channel substrate (3) preferably has a thickness that enables the formation of an adequate inclination in order to avoid cells remaining on the inclined surface of the flow channels. The upper limit of the thickness of the flow channel substrate (3) is, for example, preferably 5 mm or less, more preferably 1 mm or less and even more preferably 0.5 mm or less from the viewpoint of, for example, facilitating handling. On the other hand, the lower limit of the thickness of the flow channel substrate (3) is, for example, preferably 0.2 mm or more, more preferably 0.5 mm or more and even more preferably 1 mm or more from the viewpoints of facilitating processing and imparting strength.

Figure 5:
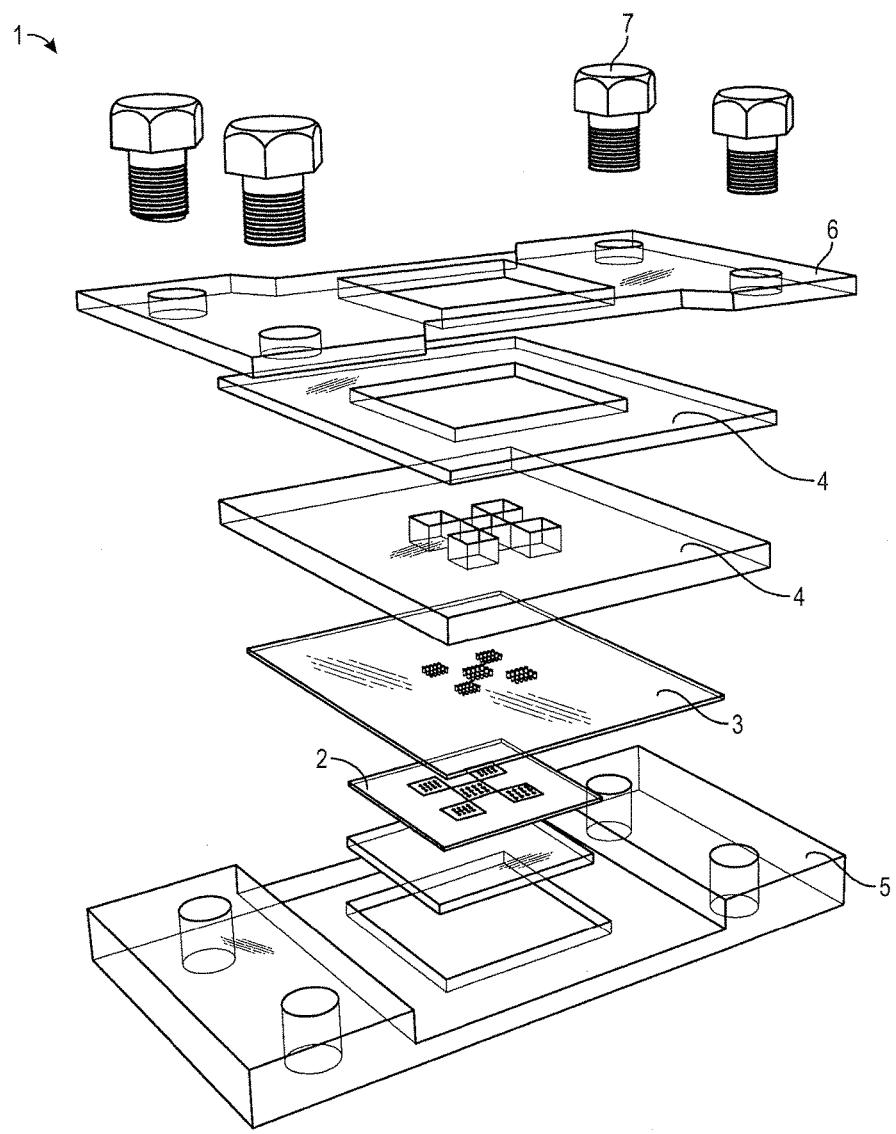
FIG. 5 is an exploded view showing one example of a cell seeding and culturing device (1).

A guide (17) may be provided on the upper surface of the flow channel substrate (3) that retains liquid by surrounding a group or all of the through holes (14), and may define a liquid storage area (18). In still another aspect, a liquid storage substrate (4) may be arranged on the upper surface of the flow channel substrate (3) to define the liquid storage area (18). In the case the liquid storage substrate (4) is superimposed on the flow channel substrate (3), the center of the liquid storage substrate (4) is cut out so as to surround a group or all of the through holes (14) on the upper surface of the flow channel substrate (3), and in the case the flow channel substrate (3) and the liquid storage substrate (4) are superimposed, the liquid storage area (18) can be configured on the side of the flow channel substrate (3) having a group or all of the through holes (14) (FIG. 1). The liquid storage substrate (4) may be composed of a plurality of substrates and may be formed so that the cutout portions differ. For example, a first liquid storage substrate (4) may have a plurality of cutout portions so as to surround groups of the through holes (14) of the flow channel substrate (3), while a second liquid storage substrate (4') may have a cutout portion formed therein so as to surround the plurality of cutout portions of the first liquid storage substrate (FIG. 5). The flow channel can be said to include the through holes (14) of the flow channel substrate (3) and the cutout portion of the liquid storage substrate (4).

Figure 2:
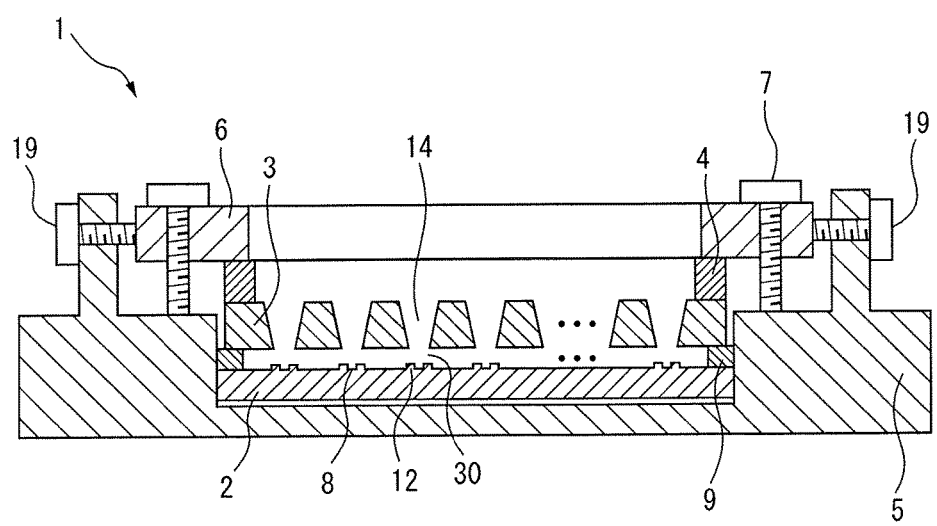
FIG. 2 is a cross-sectional schematic diagram showing on example of a cell seeding and culturing device (1).
Figure 3:
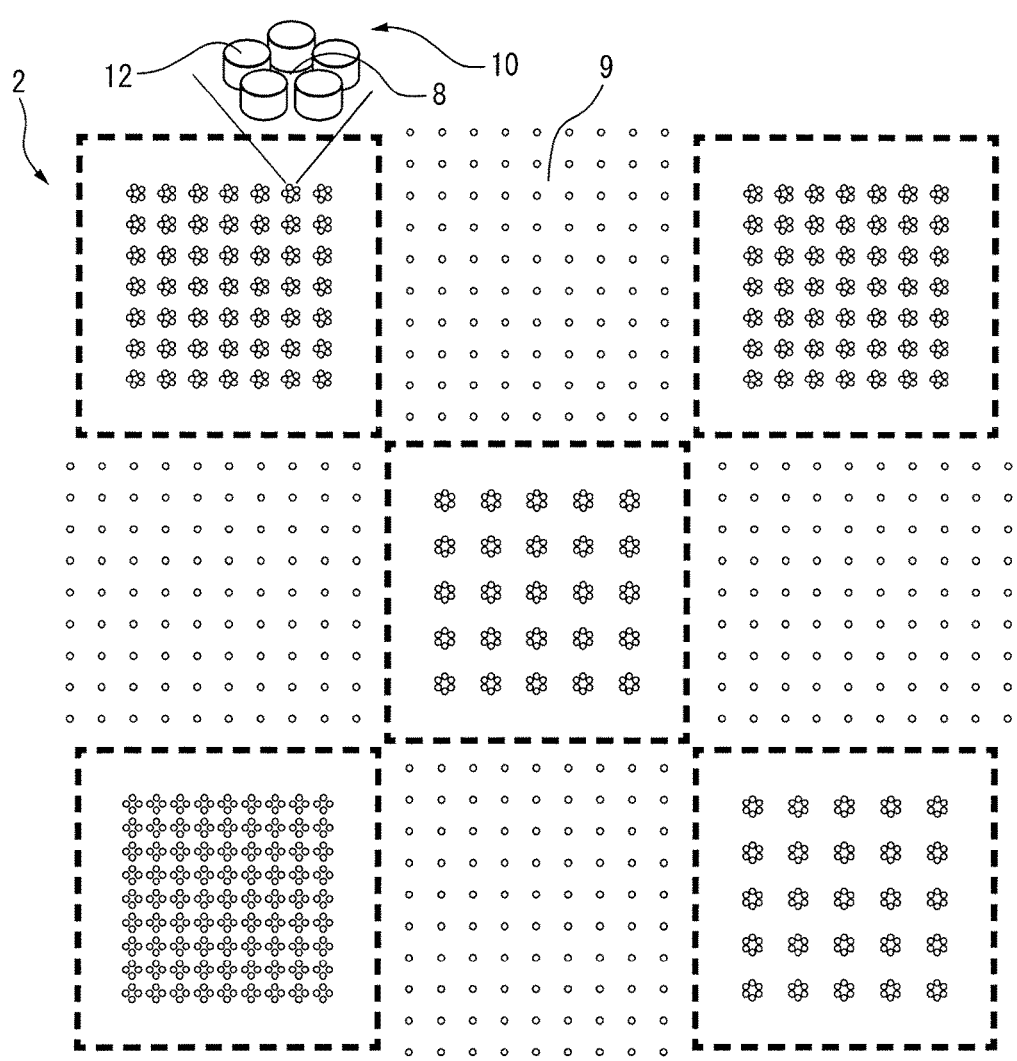
FIG. 3 is an overhead view of a cell culturing substrate (2).

The flow channel substrate (3) and the liquid storage substrate (4) are preferably adhered in advance when arranging on the cell culturing substrate (2) from the viewpoint of facilitating operation. The substrate may be adhered by plasma treatment or may be adhered using an arbitrary adhesive such as polydimethylsiloxane (PDMS). The adhered flow channel substrate (3) and liquid storage substrate (4) are arranged on the cell culturing substrate (2), are further interposed between the lower substrate immobilizing substrate (5) and the upper substrate immobilizing substrate (6), and are immobilized by the fasteners (7). While this immobilization allows manual movement of the relative positions of the flow channel substrate (3) adhered to the liquid storage substrate (4) and the substrate immobilizing substrate, the cell seeding and culturing device (1) can be tightened by the fasteners (7) to a degree that prevents a shift in relative position even if the cell seeding and culturing device (1) is merely moved or inclined. As a result, by allowing the relative positions of the flow channel components and substrate immobilizing substrates to be moved manually following immobilization, the locations of the exits (16) of the through holes (14) of the flow channel substrate (3) can be adjusted so as to overlap with the cell arrangement areas (8) of the cell culturing substrate (2). On the other hand, the cell seeding and culturing device (1) may also be further provided with a positional adjustment mechanism. Positional adjustment screws (19) can be provided as an example of a positional adjustment mechanism. For example, by adhering the flow channel substrate (3), the liquid storage substrate (4) and the upper substrate immobilizing substrate (6), and providing the positional adjustment screws (19) in the upper substrate immobilizing substrate (6) in directions in which they rotate in the X, Y and Z directions and relative to the lower substrate immobilizing substrate (5), fine positional adjustments can be made after immobilizing with the fasteners (7) (FIG. 2). Instead of providing the positional adjustment screws (19), the flow channel substrate (3) adhered to the liquid storage substrate (4) may be configured so as to protrude from the lower substrate immobilizing substrate (5) and the upper substrate immobilizing substrate (6), and the flow channel substrate (3) may be manipulated with a microscope micrometer while holding down the lower substrate immobilizing substrate (5) to make fine positional adjustments both easily and precisely.

The size of the exit (16) of each flow channel formed in the flow channel substrate is preferably smaller than the cell arrangement areas (8) or the cell retainers (10), and is, for example, preferably 50 μm or less, more preferably 40 μm or less and even more preferably 30 μm or less. On the other hand, since cells end up becoming clogged if the exits (16) are excessively small, the size of the exits (16) can be suitably set corresponding to the size of the cells, and in the case of an average cell size of 15 μm, the lower limit value of the size of the exits (16) is preferably 20 μm or more, more preferably 26 μm or more and even more preferably 30 μm or more. Although the size of the entrance (15) of each flow channel is preferably the same from the viewpoint of seeding cells at a uniform cell density, the size of the entrances (15) may also be respectively and suitably changed for the purpose of changing cell density. The entrance (15) of each flow channel can be arbitrarily set to a size that does not interfere with the entrances (15) of other flow channels, and from the viewpoint of enhancing cell utilization rate, is, for example, preferably 100 μm or more, more preferably 150 μm or more and even more preferably 200 μm or more. On the other hand, since cells end up adhering to the walls of the through holes if the slope of the inner walls of the through holes is excessively gentle, from the viewpoint of cells being unable to pass through the flow channels, the size of the entrances (15) is, for example, preferably 500 μm or less, more preferably 300 μm or less and even more preferably 200 μm or less.

In the present invention, the seeded cells may be cells of any living organism, examples of which include vertebrates such as humans, mice, monkeys or other mammals, birds, reptiles, amphibians or fish, and invertebrates such as sea urchins or sea squirts. Although the cells are preferably nerve cells, such as nerve cells acquired or cultured from a living body, nerve cells induced to differentiate from precursor cells or precursor cells of nerve cells from the viewpoint of using in cell network research, and particularly nerve cell network research, the cells are not limited thereto, but rather may also include glia cells that promote the survival of nerve cells as well as various types of muscle cells, retinal cells and olfactory cells connected to nerve cells. Nerve cell precursor cells may be arbitrary cells provided they are cells that are able to differentiate into nerve cells, and examples thereof include neural stem cells, mesenchymal stem cells, pluripotent stem cells, and particularly induced pluripotent stem (iPS) cells, embryonic stem (ES) cells and embryonic germ (EG) cells, as well as bone marrow stromal cells capable of differentiating into nerve cells. Since nerve cells are non-reproductive cells, research on diseases of the nervous system such as Parkinson's disease, Alzheimer's disease, amyotrophic lateral sclerosis, multiple sclerosis, progressive supranuclear palsy or spinocerebellar degeneration is forced to either use animal disease models or nerve cells functioning as the focus of a disease only after a patient has died, thereby resulting in the current situation of delays in treatment research. Thus, from the viewpoint of developing in vitro disease models derived from patients, it is more preferable to use human iPS cells derived from these patients, nerve cells differentiated from those cells or precursor cells thereof as seeded cells.

A cell suspension introduced into the cell seeding and culturing device of the present invention may be a suspension obtained by suspending the aforementioned cells in a cell medium, or may be a suspension obtained by replacing with a liquid capable of sustaining the cells, such as physiological saline in the manner of PBS or TBS, or water. In addition, the medium used to culture cells after cell seeding may be a desired cell culture medium. For example, a medium obtained by adding an additive such as salt, serum, antibiotics, growth factors or trace nutrients to a medium such as Eagle's medium, Dulbecco's modified eagle's medium (DMEM), Ham's F10 medium of Ham's F12 medium can be used as a cell culture medium. In the case stem cells such as iPS cells, ES cells, neural stem cells or partially differentiated cells are seeded as seeded cells and then cultured so as to cause to differentiate into desired cells such as nerve cells, a known stem cell culture broth, differentiation-inducing culture broth or nerve cell culture broth may each be different culture broths and can be sequentially replaced. Culture broth for motor neurons and glia cells is obtained by adding trace nutrients in the form of retinoic acid, sonic hedgehog or cAMP and the like to the aforementioned cell culture broths, or by adding growth factors such as insulin, transferrin, insulin-like growth factor (IGF), brain-derived neurotrophic factor (BDNF) or glia cell line-derived neurotrophic growth factor (GDNF) to the aforementioned cell culture broths.

A nerve cell network can be formed between the cell arrangement areas (8) by seeding and culturing nerve cells or precursor cells thereof. One or a plurality of cells are immobilized in the cell arrangement areas (8), and a nerve cell network can be formed mediated by synapses between cells by allowing axons or dendrites to extend from cells present in a single cell arrangement area (8) to cells present in another cell arrangement area (8).

A cell network formed on the cell culturing substrate (2) that contains cells seeded by the cell seeding and culturing device according to the present invention can be used to carry out various types of imaging research, including calcium imaging as explained below, imaging analyses by labeling presynaptic sites with a marker in the form of synaptophysin or synapsin, imaging analyses by labeling dendrites with a marker in the form of MAP2, and imaging analyses using FM1-43 or FM4-64 dye to label endosomes and exosomes.

(Calcium Imaging Analysis)

Calcium imaging refers to a technique consisting of preliminarily introducing a calcium probe (pigment emitting fluorescence coupled to calcium ions) into nerve cells and capturing a phenomenon by which calcium ions flow into the cell bodies when an action current is generated in the nerve cells as fluorescence, and enables the ion channel current of the cells to be analyzed by observing fluorescence emitted during generation of the action current or during propagation of an action potential.

Thus, by composing a nerve cell network using nerve cells introduced with a calcium probe and, for example, injecting current or applying voltage to a single nerve cell among those nerve cells, a plurality and/or large number of nerve cells can be measured by the aforementioned calcium imaging.

According to this technique, calcium imaging can be used to measure the state resulting from selecting a single nerve cell (first nerve cell) that composes a nerve cell network, stimulating that nerve cell by injecting current or applying voltage to generate an action potential, simultaneously allowing the action potential to propagate to adjacent peripheral nerve cells (second nerve cells) through the nerve cell network, and allowing the action potential to further propagate from the second nerve cells to third nerve cells adjacent thereto. In addition, a nerve cell network has synaptic current generated by spontaneous firing of nerve cells and micro-synaptic current generated by spontaneous release of neurotransmitters from the pre-synapse stage, and since calcium flows into the cells as a result thereof, the status of a network can also be analyzed by detecting calcium by calcium imaging.

Although the electrode stimulation method is an example of the prior art, in the case of this method, analysis is complicated due to the difficulty in selectively stimulating a single nerve cell. In addition, in another example of the prior art in the form of stimulation using a micropipette electrode, although a single nerve cell can be selectively stimulated, this method is difficult to adapt to the use of multiple channels required for high-throughput screening. According to the method of the present invention, the measuring unit can be made to be extremely compact, thereby facilitating the use of multiple channels.

(Imaging Analyses Using Synaptophysin and Synapsin)

Synaptophysin and synapsin are membrane proteins of synaptic vesicles, and although they are markers of presynaptic sites, pigments can be bound to these proteins by binding the pigment to these antibodies and using an antigen-antibody reaction. As a result, synaptic sites can be labeled.

(Imaging Analyses Using MAP2)

MAP2 is a dendrite marker that can be used to label dendritic sites by adding pigment to these antibodies and allowing to react.

(Imaging Analyses Using FM1-43 and FM4-64)

FM1-43 and FM4-64 have the characteristic of emitting fluorescence only when they have irreversibly entered a cell membrane and bound to the cell membrane without passing through, and can be used to label endosomes and exosomes. They also have the characteristic of being able to label cells while maintaining the vital functions of the cells.

(Optics of Imaging Analyses)

When performing imaging analyses on a cell culturing substrate that contains cells that have been seeded using the cell seeding and culturing device according to the present invention, a device is preferably used that is provided with the optics elements indicated below.

First, a light receiving device that receives light emitted by nerve cells is installed in the upper portion of the cell culturing substrate on the side of a first surface (2S) thereof. In addition, an irradiation device for irradiating nerve cells or the substrate surface with laser light and the like is installed in the upper portion of the cell culturing substrate on the side of the first surface (2S). This irradiation device is particularly preferably further equipped with collector optics for irradiating only a prescribed single cell with light.

As a result of being provided with the optics elements described above, light can be measured in both a non-contact and non-destructive manner, which in addition to enabling analyses to be performed without impairing the function of the nerve cell network, allows analyses to be performed rapidly while also enabling analyses to be performed precisely by accurately exciting a single nerve cell with the collector optics.

[Planar Patch-Clamp Device]

Figure 6:
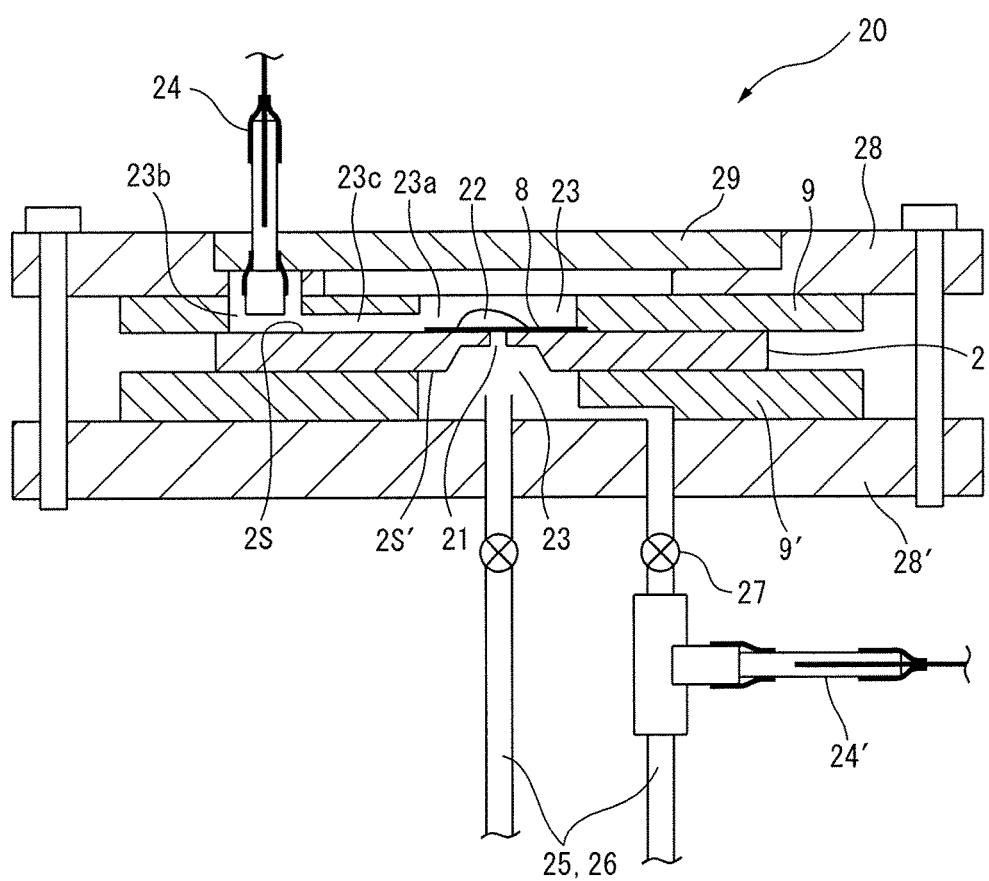
FIG. 6 is a cross-sectional view schematically showing a single-channel type planar patch-clamp device.

The planar patch-clamp method is a method that enables high-throughput screening by multi-point measurement that was difficult with the pipette patch-clamp method, and consists of providing a plurality of microscopic planar patch-clamp through holes (21) in an electrically insulated substrate, and measuring membrane potential, membrane current or other electrical changes in the cells arranged in the planar patch-clamp through holes (21) using electrodes arranged on each side of the electrically insulated substrate or imparting an electrical stimulus to the cells. An explanation is first provided of a single-channel type planar patch-clamp device (to be simply referred to as a "single-channel device") as an example of a planar patch-clamp device (20) (FIG. 6). The single-channel device is a device that has a single structural unit (referred to as a "channel") that enables measurement according to the planar patch-clamp method, and can be in the form of a multi-channel type planar patch-clamp device enabling simultaneous or sequential measurement of electrical properties by providing a plurality of channels, or a compound multi-channel planar patch-clamp device that incorporates a plurality of multi-channel type planar patch-clamp devices.

Although FIG. 6 shows a schematic cross-sectional view of the single-channel type planar patch-clamp device (single-channel device) (20), the planar patch-clamp device of the present invention is not limited to the device shown in FIG. 6. The single-channel device (20) of FIG. 6 has an electrically insulated cell culturing substrate (2) having the first surface (2S) and a second surface (2S'), this cell culturing substrate (2) is the cell culturing substrate (2) that composes the cell seeding and culturing device (1) of the present invention, and cells are arranged in cell arrangement areas by using the cell seeding and culturing device (1). The side of the cell culturing substrate (2) on which cells are arranged is defined as the first surface (2S) and the opposite side is defined as the second surface (2S'). In the case of using the cell culturing substrate (2) in a planar patch-clamp device, the planar patch-clamp through holes (21), which connect the first surface (2S) and the second surface (2S'), are preliminarily provided in the cell arrangement areas (8) of the cell culturing substrate (2). The size of the planar patch-clamp through holes (21) is set to a size that does not allow the passage of cells (22) arranged in the cell arrangement areas (8), but does allow passage of liquid. Thus, the inner diameter of the planar patch-clamp through holes (21) is suitably selected corresponding to the size of the cells (22) used. For example, although the inner diameter of the planar patch-clamp through holes (21) is preferably about 1 μm to 3 μm from the viewpoint of using nerve cells, it is not limited thereto.

The cell culturing substrate (2) used in the planar press-clamp method may be formed from a single material or may be formed by mixing or laminating a plurality of materials. As an example thereof, in the case of using a silicon substrate, a silicon substrate having a structure in which a silicon layer on the side of the first surface (2S), an intermediate silicon oxide layer, and a silicon layer on the side of the second surface (2S') are sequentially laminated (silicon-on-insulator, SOI) is preferable. In a silicon substrate employing such a laminated structure, since an extremely highly insulating intermediate layer is present between two silicon layers, a state of high resistance can be established during closure of ion channels of the cells (22) targeted for measurement, and background noise can be reduced.

In the case of using an SOI substrate, the thickness of the intermediate layer is preferably as thick as possible from the viewpoints of reducing parasitic capacitance and increasing insulation resistance. In addition, if the thickness of the intermediate layer is inadequate, capacitance may increase and resistance may decrease, thereby resulting in the potential for increased noise. Accordingly, the thickness of the intermediate layer is, for example, preferably 5 nm or more, particularly preferably 10 nm or more and more preferably 100 nm or more. On the other hand, hole forming processing may no longer be simple if the intermediately layer is excessively thick. From these viewpoints, the thickness of the intermediate layer is preferably 10 μm or less, more preferably 1 μm or less and even more preferably 500 nm or less.

A first liquid reservoir (23) communicable with the planar patch-clamp through holes (21) is provided on the side of the first surface (2S) of the electrically insulated cell culturing substrate (2). A first electrically conductive liquid (such as a buffer or culture broth referred to as a bath solution) filled around the cells (22) arranged in the cell arrangement areas (8) is retained in the first liquid reservoir (23). The first liquid reservoir (23) has a structure in which, for example, a main liquid reservoir (23a) and an auxiliary liquid reservoir (23b) are electrically connected through a liquid introduction passageway. A liquid passageway for introducing or discharging electrically conductive liquid may be provided in the first liquid reservoir (23), or the first liquid reservoir (23) may be provided with a switchable opening that is opened and closed by a cover member (29).

The first electrically conductive liquid is a liquid that enables culturing of the cells (22) arranged in the cell arrangement areas (8) and detection of electrical signals according to the patch-clamp method. For example, a cell culture broth can be used for the first electrically conductive liquid, and the culture broth can be replaced with a bath solution after culturing the cells in order to detect patch-clamp electrical signals. In addition, patch-clamp may also be carried out using the cell culture broth as is without replacing with a bath solution. An arbitrary cell culture broth or differentiation-inducing culture broth can be suitably selected for the cell culture broth corresponding to the type of cells and stage of differentiation thereof. A medium obtained by adding an additive such as salt, serum, antibiotics, growth factors or trace nutrients to a medium such as Eagle's medium, Dulbecco's modified eagle's medium (DMEM), Ham's F10 medium of Ham's F12 medium can be used for the cell culture broth. The bath solution may be any bath solution provided it is a bath solution used in the patch-clamp method. Various types of reagents may be added to the first electrically conductive liquid in order to stimulate the cells or enable imaging of the cells.

In addition, a first electrode (24) is arranged so as to attain electrical continuity with the first liquid reservoir (23) through the first electrically conductive liquid. This first electrode (24) is arranged while inserted into the first electrically conductive liquid within the first liquid reservoir (23) (such as in the auxiliary liquid reservoir (23b) thereof). In addition, a ground potential is applied to the first electrode (24), and as a result thereof, the first electrically conductive liquid in the first liquid reservoir (23) is maintained at a reference potential.

On the other hand, a second liquid reservoir (23') communicable with the planar patch-clamp through holes (21) is provided on the side of the second surface (2S') of the electrically insulated cell culturing substrate (2). A second electrically conductive liquid is retained in the second liquid reservoir (23'). The second electrically conductive liquid is a liquid that enables culturing of the cells (22) and detection of electrical signals according to the patch-clamp method. For example, a cell culture broth can be used for the second electrically conductive liquid, and the culture broth can be replaced with a buffer solution such as a pipette solution after culturing the cells in order to detect patch-clamp electrical signals. In addition, since the patch-clamp through holes are extremely minute holes, the cells (22) may also be initially cultured using a pipette solution without using a cell culture broth. The cell culture broth may be the same as the cell culture broth used for the first electrically conductive liquid, or may be a culture broth having a different composition. The pipette solution may be any arbitrary solution provided it is a pipette solution used in the patch-clamp method. Chemical substances involved in the opening and closing of ion channels or reagents used in other experiments may be dissolved in the second electrically conductive liquid. In another aspect, a second electrically conductive liquid containing cell membrane-penetrating antibiotics can be introduced into the second liquid reservoir (23') for the purpose of boring minute holes in the cell membrane. Examples of cell membrane-penetrating antibiotics include polyene-based antibiotics such as amphotericin B, nystatin or natamycin.

The first liquid reservoir (23) and second liquid reservoir (23') (which may also simply be collectively referred to as the "liquid reservoirs") can adopt an arbitrary structure provided they retain electrically conductive liquid and satisfy the requirement of arranging the electrodes (24, 24') so as to be able to maintain electrical continuity with the electrically conductive liquid. In addition, the liquid reservoirs (23, 23') may also be formed by superimposing insulating spacer members (9, 9') on the side of the first surface (2S) and/or the side of the second surface (2S') of the cell culturing substrate (2) and providing cutouts in the spacer members (9, 9') at those locations corresponding to the liquid reservoirs (23, 23'). The spacer member present on the first surface is defined as the first spacer member (9), while the spacer member present on the second surface is defined as the second spacer member (9'). Moreover, the first liquid reservoir (23) may be composed in a closed space or liquid-tight by arranging a first plate member (28) on the outermost periphery of the first spacer member (9) on the opposite side of the substrate and arranging the cover member (29) on the plate member. The second liquid reservoir (23') may also be composed to be liquid-tight by further arranging a second plate member (28') on the second spacer member (9') on the opposite side of the substrate. A liquid transport channel (25) and a liquid discharge channel (26) connected to the second liquid reservoir (23') penetrate the second plate member (28').

Although not necessarily limited thereto, the spacer members (9, 9') may any arbitrary members provided they are insulating members, and may be of the same material or different material as the electrically insulated cell culturing substrate (2). From the viewpoint of inhibiting scattered light caused by laser excitation, the first spacer member (9) on the side of the first surface (2S) is preferably composed of a light-impermeable material, while from the viewpoint of microscopic observation, the second spacer member (9') on the side of the second surface (2S') is preferably composed of an optically transparent material.

In addition, the liquid transport channel (25), which transports the second electrically conductive liquid to the second liquid reservoir (23'), and the liquid discharge channel (26), which discharges the second electrically conductive liquid from the second reservoir (23'), are connected to the second liquid reservoir (23'). The material of the liquid transport channel (25) and liquid discharge channel (26) is arbitrary, and although they can be composed with tubes made of Teflon® or vinyl chloride and the like, from the viewpoint of providing a valve (27) to be subsequently described, microchannels are preferably used that are formed by using a mold having a resist pattern formed on the surface of a silicon substrate by photolithography and transferring to polydimethylsiloxane (PDMS) or silicone rubber such as room temperature-vulcanized (RTV) silicone rubber. The use of such microchannels makes assembly of a planar patch-clamp device extremely easy, while also being able to avoid problems such as disconnection of the channels. Although the sizes of the liquid transport channel (25) and liquid discharge channel (26) are arbitrary, they have a width of 100 µm and height of about 50 µm, for example. The liquid transport channel (25) is connected to a liquid storage chamber that stores the secondary electrically conductive liquid, and the secondary electrically conductive liquid is transported through the liquid transport channel (25) by a pump arranged at an arbitrary location in the flow channel. After having been transported, the second electrically conductive liquid is discharged through the liquid discharge channel (26). The pump may be a pressure-driven pump or a suction-driven pump. Preferably, the pump is a liquid suction device arranged in the liquid discharge channel (26) that is able to apply negative pressure to the second liquid reservoir (23'). As a result of applying negative pressure, sealing of the planar patch-clamp through holes (21) by cells present in the planar patch-clamp through holes (21) can be strengthened. As a result, sealing resistance between the cells (22) and the electrically insulated cell culturing substrate (2) can be enhanced. On the other hand, in a different aspect, a whole-cell mode can be achieved by being able to apply a stronger negative pressure for the purpose of perforating the cell membrane.

In addition, the second electrode (24') is arranged so as to attain electrical continuity with the second liquid reservoir (23') through the second electrically conductive liquid. This second electrode (24') is normally provided in the liquid transport channel (25) or liquid discharge channel (26), and is arranged so as to contact the second electrically conductive liquid in the case of having introduced the second electrically conductive liquid into those channels. The resulting configuration makes it possible to measure the electrical potential of the second electrically conductive liquid in the second liquid reservoir (23') and each of the channels through the second electrode (24'). In addition, the configuration enables an arbitrary voltage to be applied to the second electrically conductive liquid in the second liquid reservoir (23') and each of the channels.

Furthermore, various types of commonly known electrodes used in conventional planar patch-clamp devices can be used for the first electrode (24) and second electrode (24') (which may also simply be collectively referred to as "electrodes"). However, in the case of a culturing type of planar patch-clamp device as described above, noise current is known to be generated easily due to fluctuations in the interfacial potential of the electrodes due to the significantly lower sealing resistance in comparison with pipette patch-clamp devices and non-culturing type planar patch-clamp devices. Accordingly, from the viewpoints of preventing fluctuations in electrode interfacial potential as much as possible and reducing noise current, the present invention preferably uses salt bridge electrodes reported by the inventors of the present invention in International Publication No. WO 2013/094418 for the electrodes.

Moreover, in the single-channel device (20) of FIG. 6, the valve (27) is provided in the liquid transport channel (25) and/or liquid discharge channel (26). This valve (27) is composed so as to be able to allow or interrupt the flow of the second electrically conductive liquid as well as allow or interrupt electrical continuity between the second liquid reservoir (23') and the second electrode (24'). Namely, in the case the valve (27) is open, flow of the second electrically conductive liquid is allowed and electrical continuity through the second electrically conductive liquid is attained, while on the other hand, in the case the valve (27) is closed, the flow of the secondary electrically conductive liquid is split and electrical continuity is interrupted according to the resistance values before and after the valve (27). Here, the valve (27) may be arranged in both the liquid transport channel (25) and liquid discharge channel (26). In this case, opening and closing of these valves (27) may be controlled collectively or individually. On the other hand, the valve (27) may only be arranged in one of the liquid transport channel (26) or liquid discharge channel (25). In this case, the second electrode (24') is provided in the channel in which the valve (27) is arranged.

Thus, the valve (27) is a non-conducting or insulating valve. More specifically, the electrical resistance value when the valve (27) is closed is, for example, preferably 1 MΩ or more, more preferably 3 MΩ or more, even more preferably 5 MΩ or more, and still more preferably 10 MΩ or more. There are no particular limitations on the upper limit value of electrical resistance.

Measurement of ion channel current of cells using the single-channel device (20) shown in FIG. 6 having the aforementioned configuration is carried out according to the procedure indicated below.

First, cells targeted for measurement are arranged in the cell arrangement areas (8) on the side of the first surface (2S) of the electrically insulated cell culturing substrate (2) so as to cover the planar patch-clamp through holes (21). In addition, the first electrically conductive liquid (such as a bath solution) is filled into the first liquid reservoir (23), and the second electrically conductive liquid (such as a pipette solution) is filled into the second liquid reservoir (23').

Continuing, minute holes are opened in the surfaces of those cell membranes in contact with the planar patch-clamp through holes (21) to create a state of electrical continuity between the insides of the cells (22) and second electrically conductive liquid (such as a pipette solution) of the second liquid reservoir (23'). Although there are no particular limitations on the technique used to put the cells (22) into the state of whole cells, an example thereof consists of preparing a solution obtained by dissolving a specific antibiotic (such as nystatin or amphotericin) in the second electrically conductive liquid and introducing the antibiotic solution into the second liquid reservoir (23') immediately prior to current measurement to allow the antibody solution to contact the cell membranes and form minute holes in the cell membranes. (In this case, after achieving the state of whole cells, the solution inside the second liquid reservoir (23') is again replaced with the second electrically conductive liquid not containing antibiotic prior to current measurement.)

Subsequently, a prescribed voltage (referred to as the membrane potential) is applied between the first electrode and the second electrode. As a result, current that passes through ion channels of the cell membranes can be recorded as channel current.

Furthermore, in the single-channel device (20) as previously explained, although the first liquid reservoir (23) is normally arranged on the upper side of the electrically insulated cell culturing substrate (2), the upper wall thereof may be configured so as to be able to be opened and closed. Subsequently, arrangement of the cells in the cell arrangement areas (8), harvesting of cells from the cell arrangement areas (8), filling and replacement of the first electrically conductive liquid, and various other treatments (such as the addition of an ion channel blocker or drug solution for investigating the drug response of the cells) can be carried out. However, similar to the second liquid reservoir (23'), the liquid transport channel (25) and liquid discharge channel (26) are also provided in the first liquid reservoir (23), and the first electrically conductive liquid may be filled and replaced using these channels.

On the other hand, filling and replacement of the second electrically conductive liquid in the second liquid reservoir (23') is carried out through the liquid transport channel (25) and liquid discharge channel (26). Namely, the second electrically conductive liquid is transported from an external supply source (not shown) through the liquid transport channel (25) and filled into the second liquid reservoir (23'). Driving of the liquid is normally carried out by providing a pump or other drive unit in the liquid transport channel (25) or liquid discharge channel (26). In addition, in the case liquid is preliminarily present in the second liquid reservoir (23'), the liquid is charged to the outside through the liquid discharge channel (26) thereby resulting in the liquid in the second liquid reservoir (23') being replaced.

Figure 7:
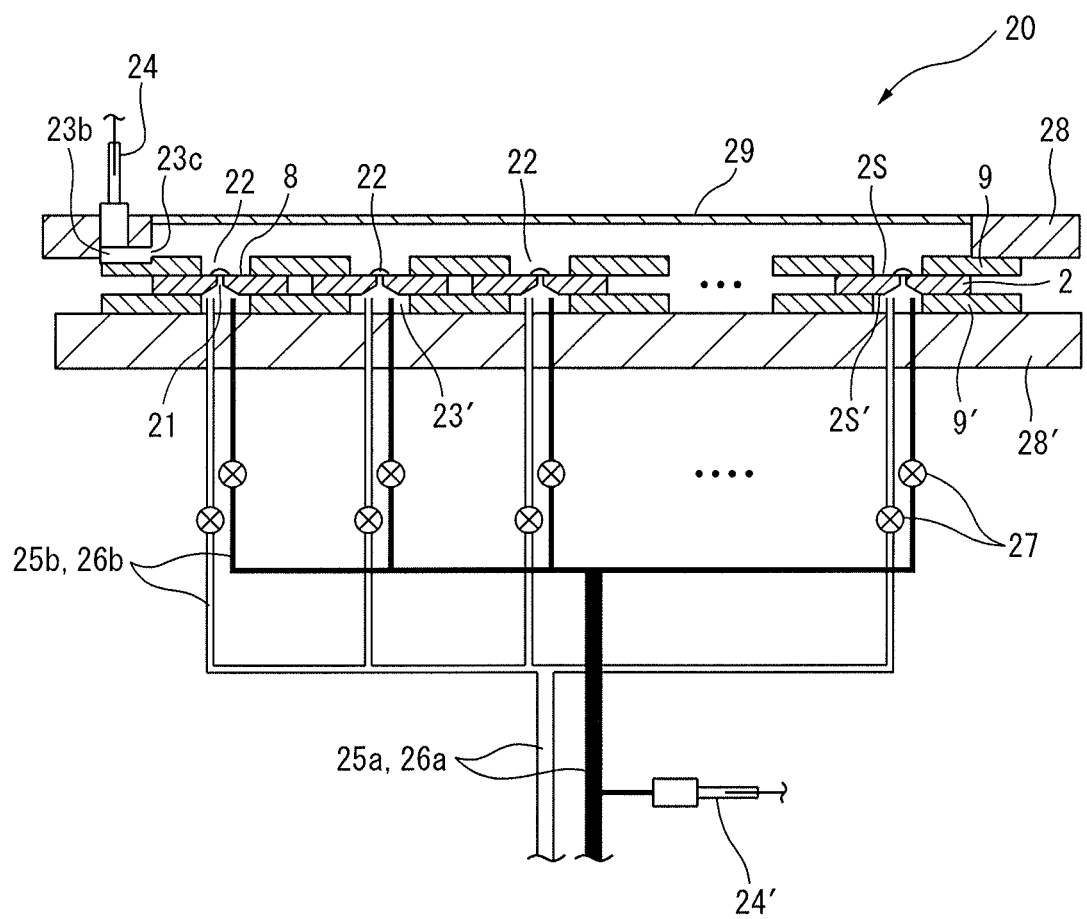
FIG. 7 is a cross-sectional view schematically showing a multi-channel type planar patch-clamp device.
Figure 8:
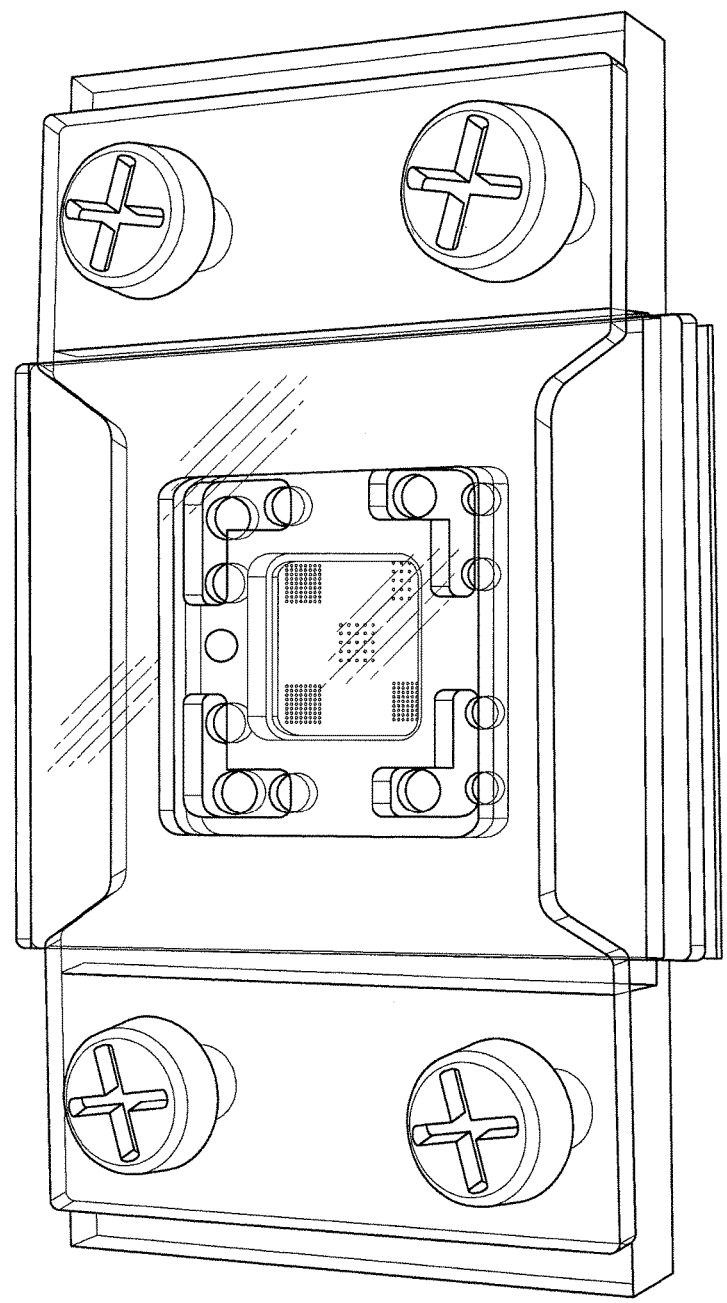
FIG. 8 is a photograph of a cell seeding and culturing device (1).

Here, in the single-channel device (20) shown in FIG. 7, together with controlling the flow or interruption of the second electrically conductive liquid by operating the valve (27) provided in the liquid transport channel (25) and/or liquid discharge channel (26), the formation or interruption of electrical continuity can be controlled between the second liquid reservoir (23') and the second electrode. As a result, leakage of liquid and current through the liquid transport channel (25) and/or liquid discharge channel (26) can be reliably prevented. Furthermore, deterioration of the electrodes caused by current leakage when measurements are not being carried out can also be prevented. In addition, replacement of the second electrically conductive liquid in the second liquid reservoir (23') becomes easier.

In the case of a culturing type of patch-clamp device, the device may be placed in an incubator and the like after arranging the cells (22) therein to culture the cells. In this case, a configuration may be employed in which the portion of the device containing the substrates (such as the portion not containing the power supply or liquid source and the like) can be separated from the device in consideration of handling ease and size restrictions when placing the device in an incubator and the like. As a result, only a portion of the device can be separated and placed in the incubator. In particular, by arranging the valve (27) on the end of the separated portion, the valve (27) can be closed during separation to prevent outflow of liquid from the channels. When measuring current, the first electrically conductive liquid (such as a bath solution) is filled in the first liquid reservoir (23), and the second electrically conductive liquid (such as a pipette solution) is filled in the second liquid reservoir (23').

[Multi-Channel Type Planar Patch-Clamp Device]

Next, an explanation is provided of a multi-channel type planar patch-clamp device that combines a plurality of single-channel devices (to be suitably abbreviated as a "multi-channel device"). A multi-channel type planar patch-clamp device is a device that has a plurality of structural units (channels) enabling measurement according to the planar patch-clamp method. The multi-channel device may be composed by providing a plurality of elements that compose the previously explained single-channel device, or as shown in FIG. 7, a multi-channel device can be composed without increasing the number of electrodes by using valves that impede electrical continuity of planar patch-clamp flow channels. However, the planar patch-clamp device of the present invention is not limited to the multi-channel device (20a) shown in FIG. 7.

The multi-channel device (20a) shown in FIG. 7 is such that the electrically insulated cell culturing substrate (2) respectively has a plurality of cell arrangement areas (8) and planar patch-clamp through holes (21) corresponding thereto. In addition, a plurality of second liquid reservoirs (23') is provided corresponding to the plurality of cell arrangement areas (8).

In addition, the liquid transport channel (25) is composed of a main liquid transport channel (25a) and a plurality of branched liquid transport channels (25b) branching from the main liquid transport channel (25a). The plurality of branched liquid transport channels (25b) are respectively connected to the plurality of second liquid reservoirs (23').

In addition, the liquid discharge channel (26) is also composed of a main liquid discharge channel (26a) and a plurality of branched liquid discharge channels (26b) branching from the main liquid discharge channel (26a). The plurality of branched liquid discharge channels (26b) are respectively connected to the plurality of second liquid retainers (23').

In addition, a second electrode (24') is provided in the main liquid transport channel (25a) and/or main liquid discharge channel (26a).

In addition, valves (27) are provided in the branched liquid transport channels (25b) and/or branched liquid discharge channels (26b) respectively connected to the plurality of second liquid reservoirs (23').

Other constituents are the same as those of the single-channel device (20) shown in FIG. 6.

Measurement of ion channel current of the cells (22) using the multi-channel device (20a) shown in FIG. 7 having the aforementioned configuration is carried out according to the procedure indicated below.

First, cells (22) targeted for measurement are respectively arranged in the plurality of cell arrangement areas (8) on the side of the first surface (2S) of the electrically insulated substrate (2) so as to cover the planar patch-clamp through holes (21). In addition, the first electrically conductive liquid (such as a bath solution) is filled into the first liquid reservoirs (23), and the second electrically conductive liquid (such as a pipette solution) is filled into the second liquid reservoirs (23').

Continuing, minute holes are opened in the surfaces of those cell membranes in contact with the planar patch-clamp through holes (21) to create a state of electrical continuity (whole cell state) between the insides of the cells and second electrically conductive liquid (such as a pipette solution) of the second liquid reservoirs (23').

Next, the valve of liquid transport channel (25) and/or liquid discharge channel (26) of the channel desired to be measured is opened while all of the other valves (27) are closed, thereby creating a state of continuity between only the cells (22) of the channel desired to be measured and the second electrode (24') through the second electrically conductive liquid.

Subsequently, a prescribed voltage (referred to as the membrane potential) is applied between the first electrode (24) and the second electrode (24'). As a result, the ion channel current of the cells (22) present in the desired channel can be recorded.

Furthermore, in the multi-channel device shown in FIG. 7, a plurality of the cell arrangement areas (8) may be present in the first liquid reservoirs (23) and a number of planar patch-clamp through holes (21) may be present corresponding to the cell arrangement areas (8). Liquid retention compartments can be partitioned by superimposing the first spacer members (9) on the side of the first surface (2S) of the substrate (2). In the case a plurality of liquid retention compartments are present, the first electrode (24) may be arranged in each of the liquid retention compartments. However, by allowing electrical continuity between the plurality of these liquid retention compartments, measurement of electrical signals or electrical stimulation can be carried out for the cells (22) of the cell arrangement areas (8) of all liquid retention compartments with a single first electrode (24). Thus, in this case, an electrically conductive member such as a metal or porous material or an insulating member may be used for the spacer member (9), and by further connecting by a sufficiently narrow pathway so as to prevent hardly any migration of liquid, electrical continuity can be attained between the liquid retention compartments. By partitioning the first liquid retainers (23) into a plurality of liquid retention compartments, since the effects on the cells of drugs added to each liquid retention compartment or response of ion channels and the like can be measured by selecting a channel to be measured by opening and closing the valves (27), the effects of a plurality of drugs can be measured in a short period of time, thereby enabling this device to be used for high throughput screening.

Although the following provides a description of examples, the cell seeding and culturing device of the present invention is not limited to the material, shape or size and so forth of the substrates used in the examples. For example, although the shape of the entrances (15) and exits (16) of the through holes (14) were square in the present example, the shape thereof may be circular as shown in FIG. 4 or rectangular provided cells can be arranged in the cell arrangement areas (8). For example, target cells can be seeded and cultured if the size of the exits (16) of the through holes is smaller than the regions of the cell arrangement areas (8), cell retainers (10) or depressions (11).

EXAMPLES

Example 1: Cell Seeding Using Cell Seeding and Culturing Device (1)

The cell seeding and culturing device (1) shown in FIG. 1 was used in the present example. A polycarbonate substrate (thickness: 0.2 mm, size: 11 mm×11 mm) was used for the cell culturing substrate (2) used in the cell seeding and culturing device (1). Columnar projections (12) (diameter: 30 μm, height: 8 μm, number of projections: 6, 4 or 5) were provided in the cell arrangement areas (8) of the cell culturing substrate (2). A polycarbonate substrate (thickness: 200 μm), provided with through holes having an entrance (15) size of 150 μm×150 μm and exit (16) size of 40 μm to 50 μm×40 μm to 50 μm, was used for the flow channel substrate (3).

The cell culturing substrate (2), flow channel substrate (3), liquid storage substrate (4), lower substrate immobilizing substrate (5) and upper substrate immobilizing substrate (6) were subjected to washing and sterilization treatment as indicated below in order to use for cell seeding. The substrates were washed 4 to 5 times by soaking for 2 hours in Haiter (Kao Corp.) followed by soaking for 30 minutes in sterile water. Subsequently, the substrates were washed 4 to 5 times by soaking overnight in Disopa disinfectant (Johnson & Johnson Inc.) and then soaking for 30 minutes in sterile water. Subsequently, the substrates were dried with an $N_2$ gas probe. Next, the surface of the cell culturing substrate (2) was coated with an extracellular matrix in the manner indicated below. The dried cell culturing substrate (2) was irradiated with plasma (Harrick Plasma, 250 mtorr to 400 mtorr, 5 minutes) followed by dropping about 120 μl of 0.01% poly-L-lysine onto the cell culturing substrate (2) and allowing to stand for 2 days in a biological clean bench. Subsequently, the cell culturing substrate (2) was washed 4 to 5 times by soaking in sterile water for 30 minutes followed by drying the cell culturing substrate (2) in a biological clean bench.

The flow channel substrate (3) and the liquid storage substrate (4) were formed into an integrated flow channel component by mutually adhering in the arrangement shown in the drawing using polydimethylsiloxane (PDMS) prior to immobilization, and flow channel components consisting of the cell culturing substrate (2), flow channel substrate (3) and liquid storage substrate (4) were superimposed with the lower substrate immobilizing substrate (5) and upper substrate immobilizing substrate (6) and immobilized with the fasteners (7). This immobilization was carried out by allowing the relative positions of the flow channel components and substrate immobilizing substrates to be moved or inclined manually, while tightening with the fasteners (7) to a degree that prevents the relative positions thereof from shifting even if the cell seeding and culturing device is merely shifted or inclined. Following immobilization, the positions of the exits (16) of the through holes (14) of the flow channel substrate (3) were adjusted so as to overlap with the cell arrangement areas (8) of the cell culturing substrate (2) by manually moving the relative positions of the flow channel components and substrate immobilizing substrates. In the present example, although the relative positions of the flow channel components and substrate immobilizing substrates were adjusted manually, positional adjustments have been confirmed to be able to be carried out easily and precisely by shifting the flow channel components using a micrometer.

100 μl to 200 μl of a rat-derived nerve cell suspension ($1 \times 10^6$ cells/ml) suspended in nerve cell culture broth (MB-X9501, Sumitomo Bakelite Co., Ltd.) were introduced into the cell seeding and culturing device (1) following positional adjustment, followed by incubating for about 12 hours and 37° C. in a $CO_2$ atmosphere until the cells were established in the cell arrangement areas (8). Following incubation, the flow channel substrate (3) was removed, nerve cells were confirmed to have become established in the cell arrangement areas (8) by microscopic observation (FIG. 9A), and a nerve cell network was formed by additionally culturing for 11 days. A microscopic image of the formed nerve cell network was photographed (FIG. 9B).

Furthermore, in the present example, there were hardly any cells present outside the cell arrangement areas (8) (FIGS. 9A and 9B). On the other hand, cells were able to be arranged outside the cell arrangement areas (8) after arranging the cells in the cell arrangement areas (8) by tightening the fasteners (7) and shifting the positions of the flow channel components. In this case, since there are no limitations on the form of the external network, a network was confirmed to be formed based on the properties of the cells per se, namely the network was self-organized. In addition, the cells are able to be separated into cell types between outside and inside the cell arrangement areas (8). For example, the seeding and culturing of motor neurons inside the cell arrangement areas (8) and glia cells or muscle cells outside the cell arrangement areas (8) may also be more effective in terms of developing disease models.

INDUSTRIAL APPLICABILITY

According to the cell seeding and culturing device (1) of the present invention, a nerve cell network can be formed in vitro by accurately arranging cells at prescribed locations. The formed nerve cell network can be used for high throughput screening according to the planar patch-clamp method or imaging method, and can be used in the fields of drug screening on nerve cells and signal analyses of neural networks.

BRIEF DESCRIPTION OF THE REFERENCE SYMBOLS

1 Cell seeding and culturing device
2 Cell culturing substrate
3 Flow channel substrate
4 Liquid storage substrate
5 Lower substrate immobilizing substrate
6 Upper substrate immobilizing substrate
7 Fastener
8 Cell arrangement area
9 Spacer member
10 Cell retainer
12 Projection
13 Groove
14 Through hole
15 Entrance
16 Exit
17 Guide
18 Liquid storage area
19 Positional adjustment screw
20 Single-channel type planar patch-clamp device
20a Multi-channel type planar patch-clamp device
21 Planar patch-clamp through hole
22 Cells
23 First liquid reservoir
23a Main liquid reservoir
23b Auxiliary liquid reservoir
23c Introducing liquid reservoir
23' Second liquid reservoir
24 First electrode
24' Second electrode
25 Liquid transport channel
26 Liquid discharge channel
25a Main liquid transport channel
26a Main liquid discharge channel
25b Branched liquid transport channel
26b Branched liquid discharge channel
27 Valve
28 First plate member
28' Second plate member
29 Cover member
30 Gap

The invention claimed is:

1. A cell seeding and culturing device capable of forming a nerve cell network, comprising:
   a cell culturing substrate having a plurality of cell arrangement areas surrounded by a plurality of projections, which inhibit cell moving and loss, and enables nerve cells to form a nerve cell network between the cell arrangement areas;
   a removable flow channel substrate having a plurality of through holes through which cells are allowed to pass, and being arranged on the culturing substrate, wherein each of the through holes defines a flow channel, wherein the upper side of the removable flow channel substrate is an entrance and the lower side of the removable flow channel substrate is an exit, wherein the flow channel is tapered from an entrance to an exit so as to seed cells, the exit of each flow channel is located above the cell arrangement areas, and the size of the exit is smaller than that of the cell arrangement area; and
   a spacer member having a thickness greater than the height of the projections, which is arranged between the culturing substrate and the removable flow channel substrate, wherein a gap which does not allow cells to flow out is formed between the exits of the flow channels and the projections.

2. The cell seeding and culturing device according to claim 1, wherein the entrance of the flow channel for seeding cells is 100-500 μm, the exit is 20-50 μm, and the thickness of the flow channel substrate is 0.2 mm-5 mm.

3. The cell seeding and culturing device according to claim 1, wherein the internal diameter of cell retainer which is configured from a plurality of projections which inhibit cell moving and loss is 10-25 μm.

4. The cell seeding and culturing device according to claim 1, wherein the height of the projections is 5-15 μm.

5. The cell seeding and culturing device according to claim 1, which enables to place one to several cells on a cell arrangement area.

6. The cell seeding and culturing device according to claim 1, wherein the removable flow channel substrate is removed from the culturing substrate after cell establishment.

7. The cell seeding and culturing device according to claim 1, wherein a spacer member having a thickness greater than the height of the projections is arranged between the culturing substrate and the removable flow channel substrate.

8. The cell seeding and culturing device according to claim 1, having a gap which enables to form a nerve cell network between the cell arrangement areas between the culturing substrate and the removable flow channel substrate, and which corresponds to the thickness of the spacer member.

9. The cell seeding and culturing device according to claim 1, further comprising a liquid storage substrate that defines a liquid storage area on the upper surface of the flow channel substrate.

10. The cell seeding and culturing device according to claim 1, wherein the culturing substrate is an electrically insulated substrate used in a planar patch-clamp method, and has through holes for the planar patch-clamp method in the cell arrangement areas that do not allow the passage of cells but allow the attaining of electrical continuity.

11. The cell seeding and culturing device according to claim 1, wherein the culturing substrate is a substrate for imaging a nerve cell network.

12. The cell seeding and culturing device according to claim 1, wherein the plurality of projections have a height of 5-15 µm, the internal diameter of the cell arrangement areas is 10-25 µm; and the removable flow channel substrate has a thickness of having 0.2 mm-5 mm, the entrance is 100-500 µm and the exit is 20-50 µm.

* * * * *